United States Patent [19]

Gaffar

[11] 4,309,410
[45] Jan. 5, 1982

[54] NON-STAINING ANTIGINGIVITIS COMPOSITION

[75] Inventor: Abdul Gaffar, Somerset, N.J.

[73] Assignee: Colgate-Palmolive Company, New York, N.Y.

[21] Appl. No.: 117,410

[22] Filed: Jan. 31, 1980

[51] Int. Cl.$^3$ ............................................... A61K 7/16
[52] U.S. Cl. ........................................ 424/57; 424/49
[58] Field of Search ..................................... 424/49–58

[56] References Cited

U.S. PATENT DOCUMENTS 3,705,103  12/1972  Cohen .................................. 252/100
3,988,433  10/1976  Benedict ............................... 424/53
4,041,149   8/1977  Gaffar et al. .......................... 424/57

FOREIGN PATENT DOCUMENTS 2208055   9/1972  Fed. Rep. of Germany.
72-01479  1/1972  Japan.
74-39818  10/1974  Japan.

OTHER PUBLICATIONS

Chem. Abstr. 83 #33030b (1975) of Iwasaki et al., Japan, 74/39818, Oct. 29, 1974.
Chem. Abstr. 78 #47669a (1973) of Okand et al., Japan, 72/01479, Jan. 14, 1972.
Chem. Abstr. 77 #143803g (1972) of Hurka Ger. Offen. 2208055, Sep. 7, 1972.

Primary Examiner—Shep K. Rose
Attorney, Agent, or Firm—H. S. Sylvester; M. M. Grill; R. L. Stone

[57] ABSTRACT

A non-antibacterial oral composition effective to promote oral hygiene containing tranexamic acid as antigingivitis agent and an additive which reduces staining of dental surfaces caused by said agent without substantially diminishing the antigingivitis activity of said agent. The antistain additive is a peroxydiphosphate salt, preferably tetrapotassium peroxydiphosphate ($K_4P_2O_8$).

9 Claims, No Drawings

NON-STAINING ANTIGINGIVITIS COMPOSITION

This invention relates to a non-antibacterial oral composition which promotes oral hygiene, and especially to such a composition for treating and controlling certain periodontal diseases, for example inflammation, bleeding and/or swelling of the gums as in gingivitis and parulis, gingival retraction, ulatrophy, etc. Types of gingivitis include afunctional gingivitis, gingivitis marginal and cotton-roll gingivitis.

Periodontitis, or pyorrhea, is a disease affecting the supporting tissues of the teeth including the gingiva, the membrane lining the sockets which the teeth lie, and the bones surrounding the teeth. The disease may initially be associated with conditions of constant irritation of the gingiva by dental plaque, food impaction, poor dental restorations, traumatic occlusion, or chemical irritants.

The gums may be seriously harmed by deposits of dental plaque, a combination of minerals and bacteria found in the mouth. The bacteria associated with plaque can secrete enzymes and endotoxins which can irritate the gums and cause an inflammatory gingivitis. As the gums become increasingly irritated by this process they have a tendency to bleed, lose their toughness and resiliency, and separate from the teeth, leaving periodontal pockets in which debris, secretions, more bacteria and toxins further accumulate. It is also possible for food to accumulate in these pockets, thereby providing nourishment for increased growth of bacteria and production of endotoxins and destructive enzymes. The pus that forms in this process is capable of destroying gum and bone tissue. A variety of bacteria are generally found to be present during the active stages of periodontal disease. Such organisms as streptocci, staphylococci and gram negatives are usually present, and are found in the purulent discharge as well as in the involved tissue, and may be absorbed into the general system through the lymphatics or venous blood stream.

The progression of the pyorrheic process usually begins with gingivitis, initiating at the margins of the gums, in which the gingiva become more tender and sensitive, and appear flabby, inflamed and swollen. Periodontal pockets become apparent, and infection takes place in these pockets. Effective control and prevention of gingivitis accordingly constitutes a desideratum for the prevention of further periodontal diseases.

A multitute of materials have been previously proposed and employed for controlling oral diseases and malfunctions such as plaque, calculus, tartar, caries, halitosis, and periodontal diseases such as gingivitis and pyorrhea, but none have been entirely satisfactory. For example some of such materials have been found to be unstable in the presence of the anionic surface active agents generally present in conventional oral preparations. A number of such materials such as the cationic quaternary ammonium agents exert an antibacterial function which undesirably tends to disrupt or destroy the normal microflora of the mouth and/or the digestive system.

Trans-4-(aminomethyl)cyclohexane-1-carboxylic acid, hereinafter referred to as tranexamic acid or TA, of the structural formula

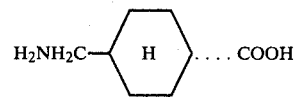

has been shown to be a highly effective agent for controlling, inhibiting or preventing gingivitis and other periodontal diseases, halitosis, and the like; see e.g. Jap. Pat. Appln. Publn. No. 39818/74. This compound is non-antibacterial and unlike antibacterials, it is a specific inhibitor of gingival inflammation, bleeding and/or swelling.

TA is a white crystalline powder having a decomposition temperature of about 380°–390° C. It has characteristic infra red absorption bands at 1637,1535 and 1383 $cm^{-1}$. It is highly soluble in water, sparingly soluble in heated ethanol, and substantially insoluble in most of the organic solvents. A method for its synthesis or its isolation from cis-trans mixtures thereof is disclosed in U.S. Pat. No. 3,499,925.

Although TA has been found to have highly desirable inhibitory functions against gingivitis and the like, it has also been found that its use in the oral cavity leads to staining or discoloration of dental surfaces, thereby seriously diminishing more widespread utilization of such functions.

It is accordingly an object of this invention to provide a TA-containing oral composition and method of use thereof which produces relatively little or no staining or discoloration of dental surfaces. Other objects and advantages will appear as the description proceeds.

The attainment of the above objects is made possible by this invention which is based upon my discovery that the inclusion of a peroxydiphosphate salt, especially tetrapotassium peroxydiphosphate, in a TA-containing oral composition prevents or inhibits the staining or discoloration of dental surfaces normally caused by the TA without substantially or significantly diminishing the antigingivitis and other desired effects of the TA.

In accordance with certain of its aspects, this invention relates to an oral composition comprising an oral (orally acceptable) vehicle, tranexamic acid (or a salt thereof) which causes dental staining, and, as anti-staining additive, an effective stain-inhibiting amount of a peroxydiphosphate salt, preferably the tetrapotassium salt ($K_4P_2O_8$).

A number of peroxy compounds are known to be effective in preventing or removing the stain from teeth. Peroxymonosulfate (Oxone) is effective in reducing the intensity of dental stain. U.S. Pat. No. 3,988,433 discloses the use of organic peroxy acids to prevent or remove stain caused by Hibitane antibacterial agent. These aforementioned substances are, however, not desirable for use in the oral cavity since they are unstable in aqueous systems and since they release active oxygen too quickly (burst effect) which tends to damage the soft tissues in the oral cavity.

In U.S. Pat. No. 4,041,149 there is disclosed and claimed the use, per se, of these same peroxydiphosphate salts for controlling and preventing mouth odor. These salts which exhibit no significant antibacterial activity, are in themselves unusually stable in aqueous media, requiring the addition of the phosphatase enzymes found in saliva in order to generate the peroxymonophosphate anion which is slowly hydrolyzed to hydrogen peroxide and orthophosphate at a rate directly proportional to the phosphatase concentration. Thus, extremely low phosphatase concentration can result in continuous generation of hydrogen peroxide and orthophosphate over a prolonged period, e.g. several months.

In addition, the peroxydiphosphate is substantive to oral surfaces and binds or reacts with the enamel surfaces of the teeth, i.e., the $Ca^{++}$ ions of the enamel, to provide for a longer lasting effect. The peroxydiphosphate has no initial burst effect of $H_2O_2$ which leads to black, hairy tongue, because it releases $H_2O_2$ at a slower rate. At equivalent concentrations of the peroxydiphosphate compound and hydrogen peroxide, it has one-tenth the amount of available oxygen compared to hydrogen peroxide. It is accordingly surprising that these peroxydiphosphates are unusually effective anti-stain additives as disclosed and claimed herein.

Any of the alkali metal peroxydiphosphates or their corresponding acid salts that are water-soluble to the extent of about 0.001 weight percent can be used in the compositions of this invention. Examples of these are potassium peroxydiphosphate ($K_4P_2O_8$), lithium peroxydiphosphate ($Li_4P_2O_8$) sodium peroxydiphosphate ($Na_4P_2O_8$), tripotassium monosodium peroxydiphosphate ($K_3NaP_2O_8$), dipotassium disodium peroxydiphosphate ($K_2Na_2P_2O_8 2H_2O$), monopotassium trisodium peroxydiphosphate ($KNa_3P_2O_8$), monopotassium monosodium dihydrogen peroxydiphosphate ($KNaH_2P_2O_8$), trilithium monopotassium peroxydiphosphate ($Li_3KP_2O_8$), dilithium dipotassium peroxydiphosphate ($Li_2K_2P_2O_8$), monolithium tripotassium peroxydiphosphate, ($LiK_3P_2O_8$), trilithium monosodium peroxydiphosphate, ($Li_3NaP_2O_8$), dilithium disodium peroxydiphosphate ($Li_2Na_2P_2O_8$), monolithium trisodium peroxydiphosphate ($Li Na_3P_2O_8$), monolithium monosodium dihydrogen peroxydiphosphate ($LiNaH_2P_2O_8$), and monolithium monopotassium dihydrogen peroxydiphosphate ($LiKH_2P_2O_8$), in addition to dizinc peroxydiphosphate ($Zn_2P_2O_8$), tetraammonium peroxydiphosphate dihydrate ($(NH_4)_4P_2O_8 2H_2O$), and the acid salts of group 2 metals such as barium dihydrogen peroxydiphosphate ($BaH_2P_2O_8$), calcium dihydrogen peroxydiphosphate ($CaH_2P_2O_8$), and the like.

The preferred tetrapotassium peroxydiphosphate is a stable, odorless, finely divided, free-flowing, white, non-hygroscopic crystalline solid having a molecular weight of 346.35 and an active oxygen content of 4.5%. The potassium peroxydiphosphate is 47–51% water-soluble at 0°–61° C., but insoluble in common solvents such as acetonitrile, alcohols, ethers, ketones, dimethyl formamide, dimethyl sulfoxide, and the like. A 2% aqueous solution has a pH of about 9.6 and a saturated solution thereof a pH of about 10.9. A 10% solution in water at 25° C. showed no active oxygen loss after four months; and at 50° C. a 10% solution showed an active oxygen loss of 3% in 6 months. This stability permits long shelf-life of oral compositions containing said peroxydiphosphate compound.

The concentration of these additives in oral compositions can range widely, typically upward from about 0.01% by weight with no upper limit except as dictated by cost or incompatibility with the vehicle. Effective and/or optimal stain-inhibiting amounts of this additive in any particular instance is readily determinable by routine experimentation. Typically, concentrations of about 0.01% to about 10%, preferably about 0.1% to 6%, more preferably about 0.3% to about 3.0%, by weight are utilized. Oral compositions which in the ordinary course of usage could be accidentally ingested preferably contain lower concentrations of these additives. Thus, a mouthwash in accordance with this invention preferably contains less than about 3 weight % of the additive, preferably about 0.5 to about 2.5 weight %. Dentifrice compositions, topical solutions and prophylactic pastes, the latter to be administered professionally, can preferably contain 1.0 to about 6 weight % of the additive. Most desirably the additive is present in a molar excess relative to the amount of TA antigingivitis agent in order to best minimize, inhibit or prevent staining.

The TA agent may be employed in free acid form or in the form of an orally acceptable salt thereof, preferably water soluble, such as with an alkali metal (e.g. Na or K), ammonium, or $C_1$–$C_{18}$ mono-, di- or tri-substituted ammonium (e.g. alkanol substituted such as mono-, di- or tri-ethanolammonium) cation. Typically, about 0.001 to about 10.0%, preferably about 0.01 to about 5.0%, and more preferably about 0.03 to about 3.0%, by weight of this TA agent are employed in the oral compositions of this invention.

In certain highly preferred forms of the invention, the oral composition may be substantially liquid in character, such as a mouthwash or rinse. In such a preparation the vehicle is typically a water-alcohol mixture. Generally, the ratio of water to alcohol is in the range of from about 1:1 to about 20:1 preferably from 3:1 to 20:1 and most preferably about 17:3, by weight. The total amount of water-alcohol mixture in this type of preparation is typically in the range of from about 70 to about 99.9% by weight of the preparation. The pH of such liquid and other preparations of the invention is generally in the range of from about 4.5 to about 9 and typically from about 5.5 to 8. The pH is preferably in the range of from about 6 to about 8.0. It is noteworthy that the compositions of the invention may be applied orally at a pH below 5 without substantially decalcifying dental enamel.

Such liquid oral preparations may also contain a surface active agent and/or a fluorine-providing compound.

In certain other desirable forms of this invention, the oral composition may be substantially solid or pasty in character, such as toothpowder, a dental tablet, a toothpaste or dental cream. The vehicle of such solid or pasty oral preparations contains polishing material. Examples of polishing materials are water-insoluble sodium metaphosphate, potassium metaphosphate, tricalcium phosphate, calcium pyrophosphate, magnesium orthophosphate, trimagnesium phosphate, calcium carbonate, alumina, hydrated alumina, aluminum silicate, zirconium silicates, silica, bentonite, and mixtures thereof. Preferred polishing materials include crystalline silica having particle sizes of up to 5 microns, a mean particle size of up to 1.1 microns, and a surface area of up to 50,000 $cm^2$/gm., silica gel, complex amorphous alkali metal aluminosilicate, hydrated alumina, dicalcium phosphate.

Alumina, particularly the hydrated alumina sold by Alcoa as C333, which has an alumina content of 64.9% by weight, a silica content of 0.008%, a ferric oxide content of 0.003%, and a moisture content of 0.37%, at 110° C., and which has a specific gravity of 2.42 and a particle size such that 100% of the particles are less than 50 microns and 84% of the particles are less than 20 microns, is particularly desirable.

When visually clear gels are employed, a polishing agent of colloidal silica, such as those sold under the trademark SYLOID as Syloid 72 and Syloid 74 or under the trademark SANTOCEL as Santocel 100 and alkali metal aluminosilicate complexes are particularly useful, since they have refractive indices close to the refractive indices of gelling agent-liquid (including water and/or humectant) systems commonly used in dentifrices.

Many of the so-called "insoluble" polishing materials are anionic in character and also include small amounts of soluble material. Thus, insoluble sodium metaphosphate may be formed in any suitable manner, as illustrated by Thorpe's Dictionary of Applied Chemistry, Volume 9, fourth Edition, pp. 510-511. The forms of insoluble sodium metaphosphate known as Madrell's salt and Kurrol's salt are further examples of suitable materials. These metaphosphate salts exhibit a minute solubility in water, and therefore are commonly referred to as insoluble metaphosphates. There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced by washing with water if desired. The insoluble alkali metal metaphosphate is typically employed in powder form of a particle size such that no more than about 1% of the material is larger than 37 microns.

The polishing material is generally present in amounts ranging from about 10 to about 99% by weight of the oral preparation. Preferably, it is present in amounts ranging from about 10 to about 75% in toothpaste, and from about 70 to about 99% in toothpowder.

In the preparation of toothpowders, it is usually sufficient to admix mechanically, e.g., by milling, the various solid ingredients in appropriate quantities and particle sizes.

In pasty oral preparations the above-defined combination of the antigingivitis agent and additive should be compatible with the other components of the preparation. Thus, in a toothpaste, the liquid vehicle may comprise water and humectant typically in an amount ranging from about 10 to about 90% by weight of the preparation. Glycerine, sorbitol, or polyethylene glycol may also be present as humectants or binders. Particularly advantageous liquid ingredients are polyethylene glycol and polypropylene glycol. Also advantageous are liquid mixtures of water, glycerine and sorbitol.

In clear gels where the refractive index is an important consideration, about 3-30% by weight of water, 0 to about 80% by weight of glycerine, and about 20-80% by weight of sorbitol is preferably employed. A gelling agent, such as natural or synthetic gums or gum-like materials, typically Irish moss, sodium carboxymethylcellulose, methyl cellulose, hydroxyethyl cellulose, gum tragacanth, polyvinylpyrrolidone, starch, and preferably hydroxypropyl methyl cellulose and the Carbopols (e.g. 934,940 and 941), etcetera is usually present in toothpaste in an amount up to about 10% by weight, preferably in the range of from about 0.5 to about 5%. In a toothpaste or gel, the liquids and solids are proportioned to form a creamy or gelled mass which is extrudable from a pressurized container or from a collapsible, e.g., aluminum or lead, tube.

The solid or pasty oral preparation which typically has a pH measured on a 20% slurry of about 4.5 to 9, generally about 5.5 to about 8 and preferably about 6 to about 8.0 may also contain a surface active agent and/or a fluorine-providing compound.

It will be understood that, as is conventional, the oral preparations are to be sold or otherwise distributed in suitable labelled packages. Thus a jar of mouthrinse will have a label describing it, in substance, as a mouthrinse or mouthwash and having directions for its use; and a toothpaste will usually be in a collapsible tube, typically aluminum or lined lead, or other squeeze dispenser for metering out the contents, having a label describing it, in substance, as a toothpaste or dental cream.

The oral compositions of this invention may contain a non-soap synthetic sufficiently water soluble organic anionic or nonionic surfactant in concentrations generally ranging from about 0.05 to about 10, preferably about 0.5 to about 5, weight percent, to promote wetting, detersive and foaming properties. U.S. Pat. No. 4,041,149 discloses such suitable anionic surfactants in col. 4, lines 31-38, and such suitable nonionic surfactants in col. 8, lines 30-68 and col. 9, lines 1-12, which passages are incorporated herein by reference thereto.

In certain forms of this invention a fluorine-providing compound is present in the oral preparation. These compounds may be slightly soluble in water or may be fully water-soluble. They are characterized by their ability to release fluoride ions in water and by substantial freedom from reaction with other compounds of the oral preparation. Among these materials are inorganic fluoride salts, such as soluble alkali metal, alkaline earth metal and heavy metal salts, for example, sodium fluoride, potassium fluoride, ammonium fluoride, Ca fluoride, a copper fluoride such as cuprous fluoride, zinc fluoride, a tin fluoride such as stannic fluoride or stannous chlorofluoride, barium fluoride, sodium fluorsilicate, ammonium fluorosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate and mixtures thereof, are preferred.

The amount of the fluorine-providing compound is dependent to some extent upon the type of compound, its solubility, and the type or oral preparation, but it must be a nontoxic amount. In a solid oral preparation, such as toothpaste or toothpowder, an amount of such compound which releases a maximum of about 1% by weight of the preparation is considered satisfactory. Any suitable minimum amount of such compound may be used, but it is preferable to employ sufficient compound to release about 0.005 to 1%, and preferably about 0.1% of fluoride ion. Typically, in the cases of alkali metal fluorides and stannous fluoride, this component is present in an amount up to about 2% by weight, based on the weight of the preparation, and preferably in the range of about 0.05 to 1%. In the case of sodium monofluorophosphate, the compound may be present in an amount up to 7.6% by weight, more typically about 0.76%.

In a liquid oral preparation such as a mouthwash, the fluorine-providing compound is typically present in an amount sufficient to release up to about 0.13%, preferably about 0.0013 to 0.1% and most preferably about 0.0013 by weight, of fluoride.

It should at this point be noted that the inclusion of a fluorine-providing compound especially MFP (sodium monofluorophosphate), in the oral compositions of this invention must be highly judicious and selective since it has been found that such inclusion often results in oral compositions which turn yellow or brown upon aging and/or storage, apparently due to the effect of the F-containing compound on the stability of the TA agent.

Various other materials may be incorporated in the oral preparations of this invention, subject to the above. Examples are whitening agents, preservatives, silicones, chlorophyll compounds, and ammoniated material such as urea, diammonium phosphate, and mixtures thereof. These adjuvants, where present, are incorporated in the preparations in amounts which do not substantially adversely affect the properties and characteristics desired.

Any suitable flavoring or sweetening material may also be employed, also subject to the above. Examples of suitable flavoring constituents are flavoring oils, e.g., oils of spearmint, peppermint, wintergreen, sassafras, clove, sage, eucalyptus, marjoram, cinnamon, lemon and orange, and methyl salicylate. Suitable sweetening agents include sucrose, lactose, maltose, sorbitol, sodium cyclamate, perillartine, APM (aspartylphenylalanine, methyl ester) and saccharin. Suitably, flavor and sweetening agents may together comprise from about 0.1 to 5% or more of the preparation.

In preparing the oral compositions of this invention comprising the above-defined combination of antigingivits agents and additive in an oral vehicle which typically includes water, it is preferred to add the additive after the other ingredients (except perhaps some of the water) are mixed or contacted with each other.

For instance, a mouthrinse or mouthwash may be prepared by mixing ethanol and water with flavoring oils, nonionic surfactant, humectant, TA antigingivitis agent, sweetener, color and then the above-defined additive, followed by additional water as desired.

A toothpaste may be prepared by forming a gel with humectant, gum or thickener such as hydroxyethyl cellulose, sweetener and adding thereto polishing agent, flavor, antigingivitis agent, additional water, and then the above-defined additive.

In the practice of this invention an oral composition according to this invention such as a mouthwash or toothpaste containing TA antigingivitis agent in an amount effective to promote oral hygiene and the defined additive in an amount effective to reduce staining of dental surfaces otherwise resulting from the presence of the antigingivitis agent, is applied regularly to dental enamel, preferably from about 5 times per week to about 3 times daily, at a pH of about 4.5 to about 9, generally about 5.5 to about 8, preferably about 6 to 8.

The following specific examples are further illustrative of the nature of the present invention, but it is understood that the invention is not limited thereto. All amounts and proportions referred to herein and the appended claims are by weight unless otherwise indicated.

Table I below illustrates the antistaining activity of the preferred $K_4P_2O_8$ additive herein. The tooth staining characteristics of an aqueous control, a 1.0 weight % TA aqueous solution, and an aqueous solution containing 1.0 wt. % TA and 2.0 wt. % of $K_4P_2O_8$ are evaluated by slurrying each with hydroxyapatite (Biogel), a specific salivary protein, a carbonyl source (e.g. acetaldehyde), and a pH 7 phosphate buffer. The mixture is shaken at 37° C. for 18 hours. The colored HAP powder is separated by filtration, dried and the color levels (in reflectance units) determined on a Gardner color difference meter.

EXAMPLE 1

TABLE I

| Aqueous solution | Reflectance | Difference-Rd |
| --- | --- | --- |
| Control | 60.7 | — |
| 1% TA | 44.9 | +15.8 |
| 1% TA + 2% $K_4P_2O_8$ | 58.2 | −13.3 (compared to TA) |

The results shown in TABLE I show the surprising effectiveness of the peroxydiphosphate salt additives employed herein for inhibiting dental staining ordinarily produced by TA.

EXAMPLE 2

40 pure bred beagle dogs 15 to 24 months old were anesthetized (Na-Nembutal) and given complete prophylaxis, that is, removal by scaling of hard and calcified deposits on the surfaces of teeth followed by polishing with pumice. A disclosing solution (Erythrosine-Provident Hoyt lab) was used to insure the complete removal of soft and hard deposits. The animals were kept on soft diet—a ground Purina dog chow soaked in water to form soft mush. No hard substances were permitted during the study. The animals were divided into 4 groups, each group treated twice daily with test solution. The solution being tested was applied by gently spraying (with a spray bottle) all surfaces of dentition. The mouth of each dog was kept closed for 1 minute to allow the contact of the solution with dentition. Approximately 5–6 ml. of solution was applied per treatment. The treatment continued 5 days/week for the 6 week duration of the experiment.

The study was double blind. Plaque and gingivitis formation was assessed on teeth $P^4$, $P^3$, $P^2$, $C\,I^1$, $P_4$, $P_3$, $P_2\,I_1$ on the left and right side by the method of Loe and Silness. A disclosing solution was used to visualize the plaque. Gingival bleeding was evaluated by applying gentle finger pressure on the gingivae.

TABLE II below shows the results of the test with the indicated solutions.

TABLE II

| AQUEOUS SOLUTION | PLAQUE | STAIN | GINGIVITIS | NO. OF BLEEDING SITES/TOTAL SITES AT RISK |
| --- | --- | --- | --- | --- |
| Placebo (deionized water) | 2.00 ± 0.24 | 0.26 ± 0.15 | 1.25 ± 0.24 | 53/200 |
| 1% TA solution | 2.00 ± 0.23 | 0.52 ± 0.21 | 1.07 ± 0.12 | 14/190 |
| 2% $K_4P_2O_8$ | 1.80 ± 0.27 | 0.29 ± 0.18 | 1.0 ± 0.05 | 4/200 |
| 1% TA 2% $K_4P_2O_8$ | 1.90 ± 0.14 | 0.27 ± 0.15 | 0.97 ± 0.26 | 4/200 |

The results shown in TABLE II show the surprising effectiveness of the instant additives for inhibiting dental staining ordinarily produced by TA without decreasing antigingivitis activity. The additives in fact substantially reduce further gingival bleeding.

EXAMPLE 3

| | Wt. Percent |
| --- | --- |
| Hydroxypropyl methyl cellulose | 2 |
| Alumina (hydrated) | 49.0 |
| Polyethylene glycol 600 | 33.3 |

-continued

| | Wt. Percent |
|---|---|
| Sodium benzoate | 0.5 |
| Sodium saccharin | 0.2 |
| Sodium lauryl sulfate | 1.5 |
| $K_4P_2O_8$ | 3.0 |
| Tranexamic acid | 1.0 |
| Flavor* | 1.0 |
| Water to make 100% | |

*About 60% methyl salicylate, 32% menthol, 3% eugenol and 5% cineol.

EXAMPLE 4

| | Wt. Percent |
|---|---|
| Insoluble metaphosphate | 48.0 |
| Polyethylene glycol 600 | 35.8 |
| Sodium benzoate | 0.5 |
| Sodium saccharin | 0.2 |
| Sodium laurylsulfate | 1.5 |
| Flavor* | 1.0 |
| Colloidal silica | 6.0 |
| $K_4P_2O_8$ | 3 |
| Tranexamic acid | 1.0 |
| Water to make | 100% |

*About 60% methyl salicylate, 32% menthol, 3% eugenol and 5% cineol.

Examples 3 and 4 illustrate dentifrice formulations with reduced staining according to the invention. Other conventional components may be substituted or added as disclosed hereinbefore; e.g. polyethylene glycol 600 may be replaced by other gelling agents such as Pluronic F-127 (polyoxyethylenated polyoxypropylene), Laponite (Mg-Al-Si clay), or Carbopol 940.

This invention has been disclosed with respect to preferred embodiments, and it will be understood that modifications thereof obvious to those skilled in the art are to be included within the spirit and purview of this application and the scope of the appended claims.

What is claimed is:

1. An oral composition comprising an oral vehicle, tranexamic acid as non-antibacterial antigingivitis agent, whose use has been observed to lead to staining or discoloration of dental surfaces, and as anti-staining additive, an effective stain-inhibiting amount of a peroxydiphosphate salt.

2. The oral composition of claim 1 wherein said additive is tetrapotassium peroxydiphosphate.

3. The oral composition of claims 1 or 2 containing about 0.001 to about 10.0 wt. % of said non-antibacterial antigingivitis agent and about 0.01 to about 10.0 wt. % of said additive.

4. The oral composition of claims 1 or 2 containing about 0.03 to about 3.0 wt. % of said antigingivitis agent and about 0.3 to about 3.0 wt. % of said additive.

5. The oral composition of claims 1 or 2 wherein said vehicle is an aqueous-alcohol and said composition is a mouthwash of pH of about 4.5 to about 9.

6. The oral composition of claims 1 or 2 wherein said vehicle comprises a liquid vehicle and a gelling agent and a dentally acceptable polishing material is present and said composition is a toothpaste of pH of about 4.5 to about 9.

7. The mouthwash composition of claim 5 containing about 0.03 to about 3.0 wt. % of said antigingivitis agent and about 0.3 to about 3.0 wt. % of said additive.

8. The toothpaste composition of claim 6 containing about 0.03 to about 3.0 wt. % of said antigingivitis agent and about 0.3 to about 3.0 wt. % of said additive.

9. A method of improving oral hygiene comprising applying to the oral cavity an effective amount of an oral composition as defined in claims 1 or 2.

* * * * *